United States Patent
Bense et al.

(10) Patent No.: US 9,976,967 B2
(45) Date of Patent: May 22, 2018

(54) SYSTEM FOR DETECTING DEFECTS ON AN OBJECT

(71) Applicant: SNECMA, Paris (FR)

(72) Inventors: William Bense, Melun (FR); Valerio Gerez, Yerres (FR)

(73) Assignee: SNECMA, Paris (FR)

( * ) Notice: Subject to any disclaimer, the term of this patent is extended or adjusted under 35 U.S.C. 154(b) by 206 days.

(21) Appl. No.: 14/781,181

(22) PCT Filed: Mar. 27, 2014

(86) PCT No.: PCT/FR2014/050730
§ 371 (c)(1),
(2) Date: Sep. 29, 2015

(87) PCT Pub. No.: WO2014/155011
PCT Pub. Date: Oct. 2, 2014

(65) Prior Publication Data
US 2016/0054233 A1    Feb. 25, 2016

(30) Foreign Application Priority Data

Mar. 29, 2013 (FR) .................... 13 52859
Mar. 29, 2013 (FR) .................... 13 52860

(51) Int. Cl.
*G01N 21/88* (2006.01)
*G01N 25/72* (2006.01)
(Continued)

(52) U.S. Cl.
CPC ........ *G01N 21/8851* (2013.01); *G01J 5/0022* (2013.01); *G01J 5/10* (2013.01);
(Continued)

(58) Field of Classification Search
CPC .................................................. G01N 21/8851
See application file for complete search history.

(56) References Cited

U.S. PATENT DOCUMENTS 5,245,424 A    9/1993   Yoshida et al.
6,512,843 B1   1/2003   Kuwabara et al.
(Continued)

FOREIGN PATENT DOCUMENTS

DE    10 2010 032 241 A1    1/2012
FR       2 815 123 A1       4/2002
(Continued)

OTHER PUBLICATIONS

T. Maffren, et al., "Crack detection in high-pressure turbine blades with flying spot active thermography in the SWIR range", AIP Conference Proceedings, vol. 1430, Total 8 Pages, (2012), XP_55079338A.
(Continued)

*Primary Examiner* — David Porta
*Assistant Examiner* — Hugh H Maupin
(74) *Attorney, Agent, or Firm* — Oblon, McClelland, Maier & Neustadt, L.L.P.

(57) ABSTRACT

A system and method for detecting defects on an object including forming an image representing the object from signals relating to the object, constructing subdivisions of the image according to auto-adaptive resolutions, and calculating differentials between various subdivisions in order to detect an abnormal subdivision indicating incipient failure.

12 Claims, 10 Drawing Sheets

(51) Int. Cl.
    *G01N 29/44*     (2006.01)
    *G06T 7/00*     (2017.01)
    *G01J 5/00*     (2006.01)
    *G01J 5/10*     (2006.01)
    *G01N 29/04*     (2006.01)

(52) U.S. Cl.
CPC .......... *G01N 25/72* (2013.01); *G01N 29/043* (2013.01); *G01N 29/4409* (2013.01); *G06T 7/0004* (2013.01); *G01J 2005/0077* (2013.01); *G01J 2005/0081* (2013.01); *G01N 2021/8887* (2013.01); *G01N 2291/0289* (2013.01); *G01N 2291/044* (2013.01); *G01N 2291/2693* (2013.01); *G01N 2291/2694* (2013.01); *G06T 2207/20021* (2013.01); *G06T 2207/30164* (2013.01)

(56) References Cited

U.S. PATENT DOCUMENTS

| | | |
|---|---|---|
| 2002/0059831 A1 | 5/2002 | Naudet et al. |
| 2004/0217289 A1 | 11/2004 | Raulerson et al. |
| 2006/0078193 A1* | 4/2006 | Brummel ........... G01N 21/8806 382/152 |
| 2006/0151703 A1 | 7/2006 | Raulerson et al. |
| 2007/0098245 A1* | 5/2007 | Mylaraswamy ... G01N 21/8851 382/141 |
| 2007/0250245 A1 | 10/2007 | Van Der Merwe et al. |
| 2008/0000299 A1 | 1/2008 | Georgeson |
| 2010/0019153 A1 | 1/2010 | Zalameda et al. |
| 2011/0222754 A1 | 9/2011 | Zhao et al. |

FOREIGN PATENT DOCUMENTS

| | | |
|---|---|---|
| GB | 2 161 602 A | 1/1986 |
| JP | 4-240557 | 8/1992 |
| JP | 2002-195917 | 7/2002 |
| JP | 4392349 | 10/2009 |

OTHER PUBLICATIONS

Jos Willems, et al., "Aufschlussreiche Hotspots—Thermografische Prufung von industriellen Gasturbinenteilen", Panorama, Sulzer Technical Review, pp. 26-29, (2012), XP055079314.

International Search Report dated Jul. 10, 2014 in PCT/FR14/050730 Filed Mar. 27, 2014.

French Search Report dated Dec. 12, 2013 in French Application 1352860 Filed Mar. 29, 2013.

French Search Report dated Sep. 16, 2013 in French Application 1352859 Filed Mar. 29, 2013.

Japanese Office Acton dated Nov. 21, 2017 in Japanese Application No. 2016-504727, citing documents AO, AP and AQ therein, 6 pages.

\* cited by examiner

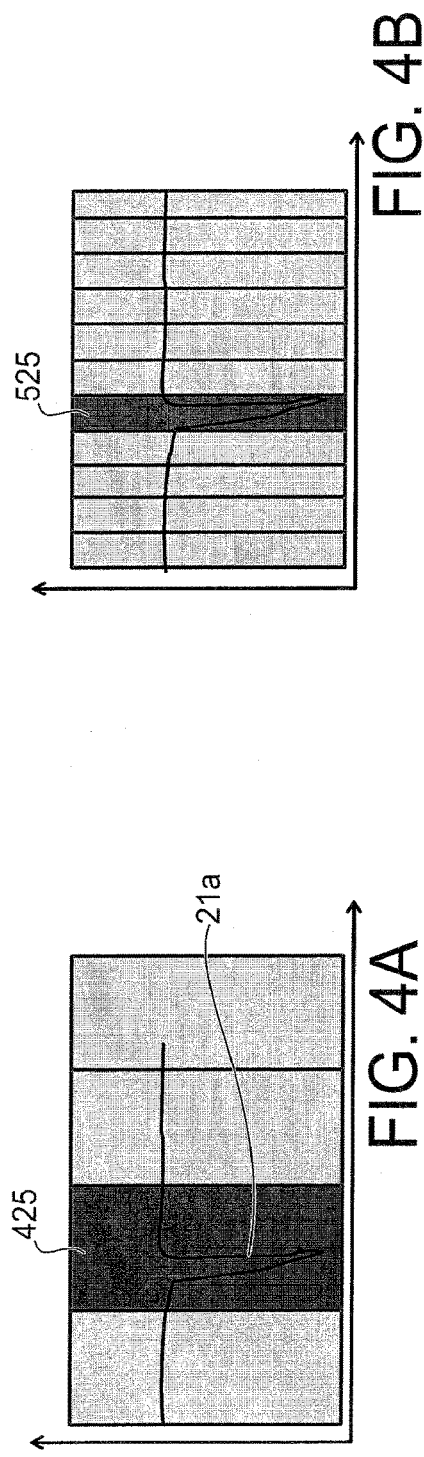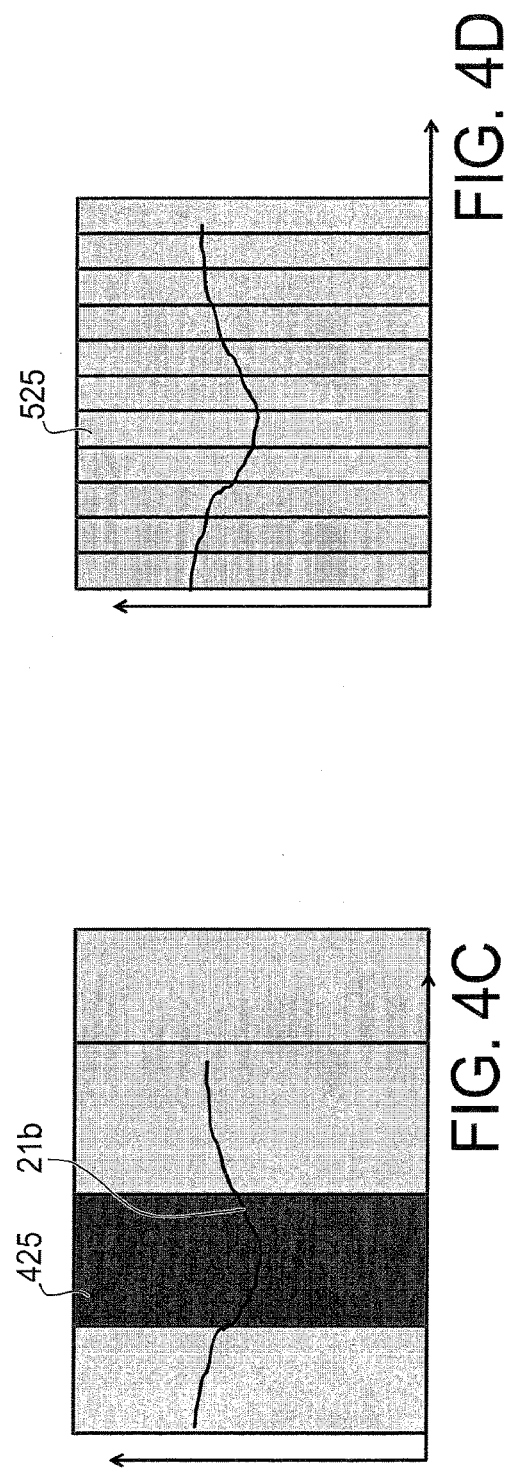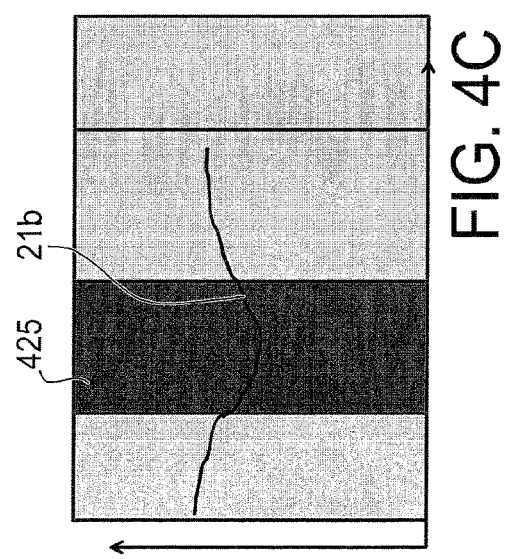

SYSTEM FOR DETECTING DEFECTS ON AN OBJECT

TECHNICAL FIELD

The present invention concerns the field of detecting defects on an object and more particularly for monitoring rotating elements of an aircraft engine.

PRIOR ART

There exist numerous techniques using optical or audible methods for detecting defects on an object. The advantage of these techniques is that they can be used in a non-intrusive manner.

For example, in the aeronautical field, during production tests or inspections of the vanes of an engine, various non-destructive inspection techniques based on the use of thermal cameras are applied. These techniques consist of using a movable heat emitter for heating the vane and a movable thermal camera for taking an infrared image of the vane. Analysis of the image is based on a comparison of a very high number of regions of the image in order to detect defects in the blade.

Thus the current methods require making calculations that may take a not insignificant amount of time, unless particularly powerful and very expensive computers are used.

Furthermore, it is difficult to know what grain to adopt (i.e. what is the resolution of the region to be compared) when the defects that are being sought are not known.

The subject matter of the present invention is consequently proposing a detection method that is simple to implement without using complex computations and capable of quickly and precisely detecting defects on an object or a component of an engine without having the aforementioned drawbacks.

DISCLOSURE OF THE INVENTION

The present invention is defined by a method for detecting defects on an object, comprising the following steps:
  forming an image representing said object from signals relating to the object,
  constructing subdivisions of said image according to auto-adaptive resolutions, and
  calculating differentials between various subdivisions in order to detect an abnormal subdivision indicating incipient failure.

The method makes it possible to detect defects of practically all sizes within a reasonable time.

Advantageously, the method comprises a confirmation phase comprising a comparison of the differentials relating to an abnormal subdivision belonging to the last image with differentials relating to the same abnormal subdivision belonging to each of a given number of previous images of said object.

This makes it possible to confirm the detection of defects while avoiding false alarms.

Advantageously, the method comprises:
  generating an alert of high or very high importance if it is found that the differentials have increased during the last images, and
  generating an alert of medium performance if it is found that the differentials remain constant during the last images.

This makes it possible to evaluate the importance of the incipient failure or defects.

According to a preferred embodiment of the invention the steps of construction of the subdivisions and of calculation of the differentials comprise the following steps:
  (a1) constructing a grid on said image in a plurality of current subdivisions,
  (a2) calculating the first current differentials between each current subdivision and adjacent current subdivisions,
  (a3) checking whether there exists a current subdivision for which first current differentials with at least a first given number of adjacent subdivisions indicate an abnormality,
  (a4) calculating, should the previous step (a3) be confirmed, second current differentials between said current subdivision and distant current subdivisions,
  (a5) checking whether said current subdivision has, with at least a second given number of distant current subdivisions, second current differentials indicating an abnormality,
  (a6) declaring said current subdivision to be invalid should the previous step (a5) be confirmed,
  (a7) reconstructing a grid on a region covering said invalid current subdivision in order to form new subdivisions overlapping the previous invalid subdivision, the new subdivisions being considered to be the actual current subdivisions,
  (a8) repeating steps (a2)-(a6) for each of the new current subdivisions of said overlap zone,
  (a9) making a mask according to a logic AND operation in said overlap zone between the previous invalid subdivisions and the new subdivisions, thus forming subdivisions with reduced sizes comprising at least one invalid subdivision, said subdivisions with reduced sizes being considered to be the actual current subdivisions,
  (a10) checking whether the size of the actual current subdivision is greater than a predetermined resolution, and
  (a11) reiterating, should the previous step (a10) be confirmed, the previous steps (a2)-(a10) for each actual current subdivision, or otherwise declaring the invalid current subdivision or subdivisions to be an abnormal subdivision or subdivisions.

Thus this method is based on zooms and an optimum number of relevant comparisons reducing the computing load and not prejudging the size of the defect beyond the resolution.

Advantageously, it is checked at step (a3) whether the first current differentials are higher than a first predetermined threshold, and at step (a5) it is checked whether the second current differentials are higher than a second given threshold.

This makes it possible, in detecting defects, to take into account any errors as well as any differences in context between distant regions.

Advantageously, the method comprises a construction of a learning database recording the sound differentials between various subdivisions of the image and at step (a3) the differences are calculated between the first current differentials and the corresponding sound differentials in order to check whether they are higher than a predetermined level and at step (a5) the differences are calculated between the second current differentials and the corresponding sound differentials in order to check whether they are higher than a second predetermined level.

This makes it possible to take account of any unevenness that may exist within the object.

Advantageously, said object is a rotating element of an aircraft engine.

This is because the digital processing according to the invention is inexpensive in computing time and can therefore easily be implemented by processing means installed in an aircraft.

According to one embodiment, the signals relating to said object are infrared signals coming from the object so that said image representing said object is an infrared image representing a transient thermal field after the heating of the object by a thermal stressing.

According to another embodiment, the signals relating to said object are ultrasound signals coming from the object so that said image representing said object is an image representing the ultrasonic waves reflected by the object.

The invention also relates to a system for detecting defects on at least one rotating element of an aircraft engine, comprising:
  onboard excitation means installed so as to cause the emission of signals by said rotating element,
  onboard acquisition means installed so as to acquire the signal sent by said rotating element, and
  processing means configured so as to perform the steps of the method according to any one of the preceding claims.

According to a first embodiment of the system according to the invention, the excitation means are heating means for heating said rotating element of the engine by means of a thermal stressing, and the acquisition means are thermographic means for acquiring an infrared image representing a transient thermal field of said rotating element.

According to a second embodiment of the system according to the invention, the excitation means are means for emitting ultrasonic waves, and the acquisition means are means for receiving ultrasonic waves reflected by the object.

The invention also relates to an automatic system for detecting defects on at least one rotating element of an aircraft engine, comprising:
  onboard heating means installed for heating said rotating element of the engine by means of a thermal stressing,
  onboard thermographic means installed so as to acquire at least one infrared image representing a transient thermal field of said rotating element, and
  processing means for computing the differentials relating to a component of the thermal field between various subdivisions of said image in order to detect variations in said component of the thermal field indicative of defects on said rotating element.

Thus it is possible to monitor the rotating elements of the engine at each flight automatically in order to detect the first signs of fatigue. This makes it possible to carry out predictive maintenance rather than simply preventive maintenance since it is possible to change the rotating elements when they truly suffer damage, thus increasing profitability (fewer parts changed) and safety (less risk of loss of blades). The analysis is carried out according to differential measurements that make it possible to be free from the context. In particular, making comparisons between spatially close regions avoids problems due to the distance of the source of heat or illumination by the sun.

Advantageously, when the differential corresponding to a current subdivision indicates an abnormality, the processing means are configured so as to compute other differentials by reorganising the subdivisions and/or refining the current comparison subdivision in order to locate the positions of the defects.

This makes it possible to reduce the number of subdivisions to be studied and consequently to reduce the computing time and the workload of a computer.

Advantageously, the processing means are configured so as to record, at each flight, said differentials relating to the thermal fields of the various subdivisions and to analyse the change in said differentials from flight to flight.

This makes it possible to consolidate the result of the detection and to systematically monitor the soundness of the rotating elements from flight to flight.

Advantageously, the detection system comprises a database of degradation signatures representing various forms of degradation and how advanced they are, and the processing means are configured so as to compare the differentials relating to the thermal fields of the subdivisions having defects with said degradation signatures.

This makes it possible to determine the most probable type of defect.

According to an advantageous embodiment of the present invention, the heating means consist of at least one anti-frost heating element already existing in the engine.

This reduces the installed mass and also makes it possible to monitor the heating means itself.

According to a variant, the heating means are intended to heat said element by means of thermal pulses.

Thus the rotating element can be heated in a sufficiently short time for the material of the rotating element not to reach a constant temperature.

According to this variant, the processing means are configured to calculate differentials between an amplitude of the thermal field of a current subdivision and amplitudes of the thermal fields of the adjacent subdivisions.

According to another variant, the heating means are intended to heat said element by means of periodic thermal waves.

According to this other variant, the processing means are configured to compute phase differences between the thermal field of a current subdivision and the thermal fields of the adjacent subdivisions.

The detection according to phase difference has the advantage of being little influenced by the distance of the heat source or the illumination from the sun, since it is not the temperature that is measured but the phase difference.

Advantageously, the rotating element is a vane of a bladed wheel of said engine.

BRIEF DESCRIPTION OF THE DRAWINGS

Other features and advantages of the invention will emerge from a reading of preferential embodiments of the invention given with reference to the accompanying drawings, among which:

FIGS. 4a-4d illustrate the detection of punctiform progressive defects on various grids, according to the invention;

DETAILED DISCLOSURE OF PARTICULAR EMBODIMENTS

The concept at the basis of the invention is based on a method for detecting defects in an object using an image representing the object and making a minimal number of comparisons between areas, the size of which adapts iteratively to the size of the defects.

Figure 1:
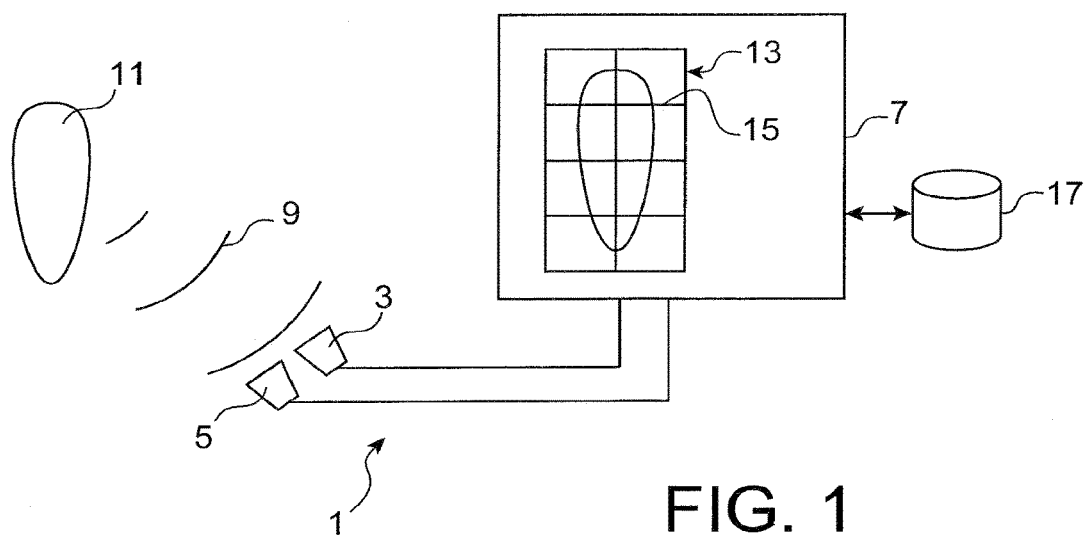
FIG. 1 illustrates schematically a system for detecting defects on an object, according to the invention.

FIG. 1 illustrates schematically a system for detecting defects on an object, according to the invention.

The detection system 1 comprises excitation means 3, acquisition means 5 and data processing means 7.

The excitation means are intended to cause the sending of signals 9 by the object 11 while the acquisition means 5 are intended to acquire these signals.

Figure 7:
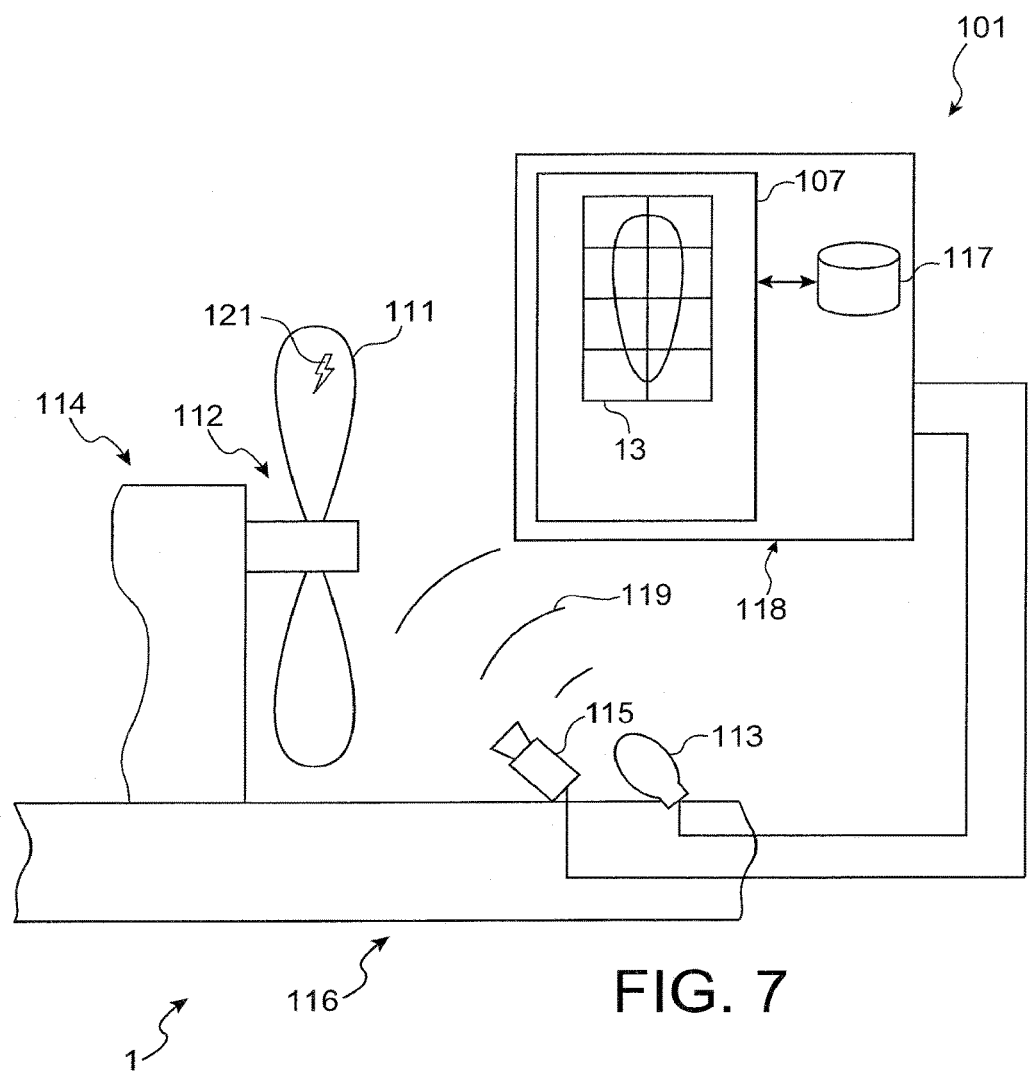
FIG. 7 illustrates schematically a system for detecting defects on a rotating element of an aircraft engine, according to a first embodiment of the system in FIG. 1.

By way of example, the excitation means 3 are heating means for heating the object 11 by thermal stressing and the acquisition means 5 are thermographic means for acquiring an infrared image representing a transient thermal field (see FIG. 7).

Figure 9:
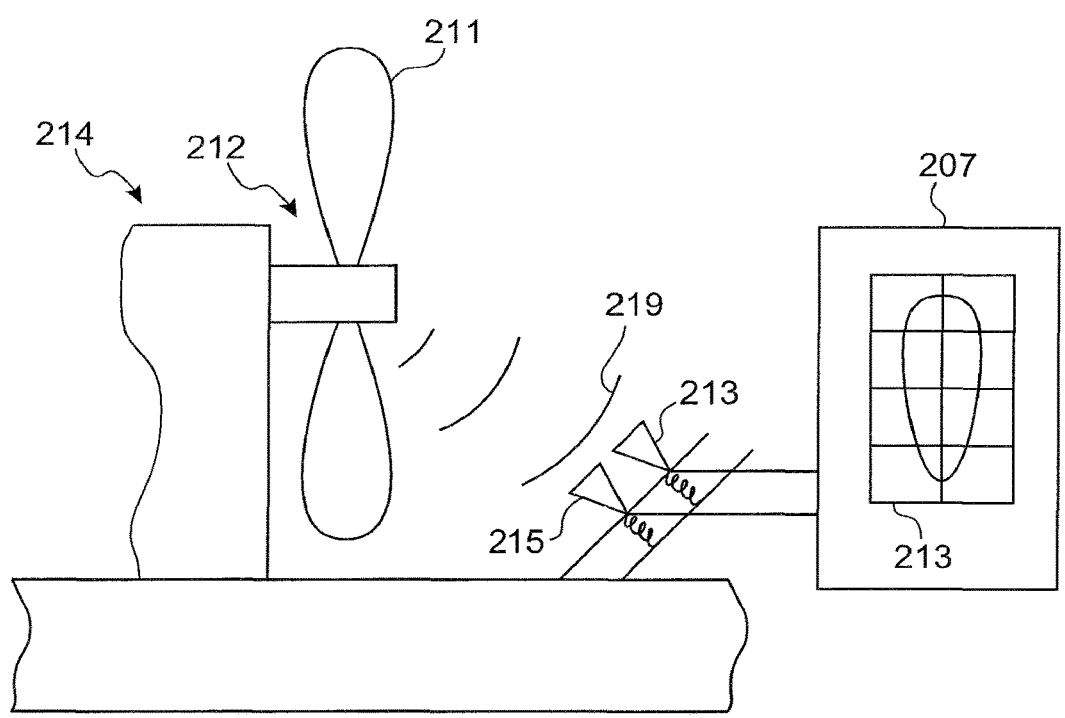
FIG. 9 illustrates schematically a system for detecting defects on a rotating element of an aircraft engine, according to a second embodiment of the system in FIG. 1.

According to another example, the excitation means 3 are means for emitting ultrasonic waves and the acquisition means 5 are means for receiving ultrasonic waves reflected by the objet 11 (see FIG. 9).

The processing means 7 are intended to process the signals 9 relating to the object in order to detect defects and generate alerts.

More particularly, the processing means 7 are configured so as to form a graph or an image 13 representing the object 11 from signals 9 relating to the object. The image 13 is defined here as a representation of an object 11 in the numerical or mathematical sense of the term where each point on the image 13 corresponds to antecedent of the object 11. Thus the image may correspond for example to an optical, thermal or acoustic representation of the object 11.

The processing means 7 are also configured to iteratively construct subdivisions of the image 13 according to autoadaptive resolutions, that is to say according to resolutions that adapt to the extent of defect.

Furthermore, the processing means 7 are configured to iteratively calculate differentials between various subdivisions in order to detect an abnormal subdivision indicative of incipient failure.

Figure 2:
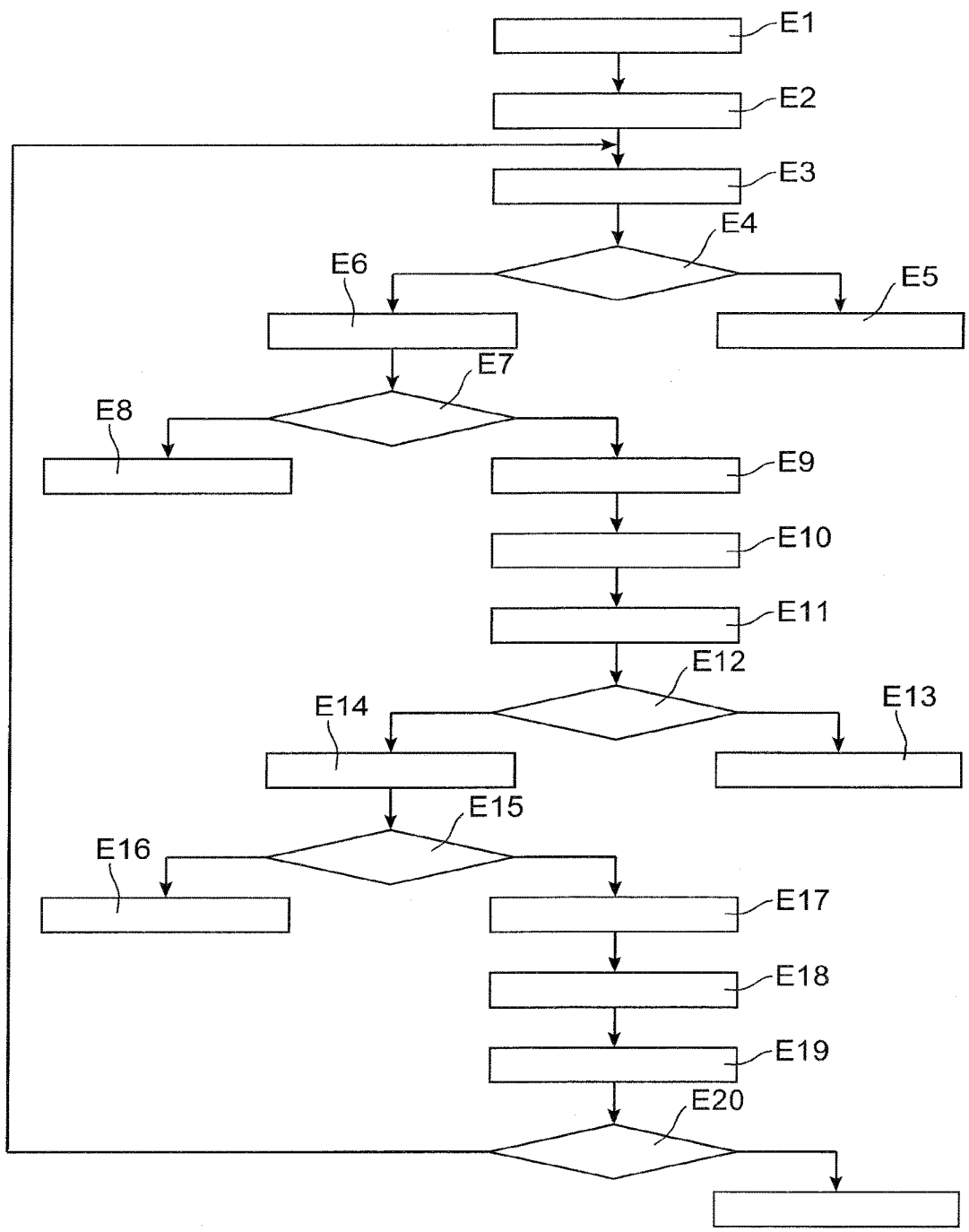
FIG. 2 is an algorithm illustrating various steps of a detection method according to a preferred embodiment of the invention.

FIG. 2 is an algorithm illustrating various steps of a detection method according to an embodiment of the invention.

Furthermore, FIGS. 3A-3E are grids on an image 13 schematically illustrating the steps of the flow diagram in FIG. 2.

At step E1 the processing means 7 are configured to form the image 13 representing the object 11 from signals 9 relating to this object. The image 13 may for example be the representation of a thermal field acquired by thermographic means or the representation of ultrasonic signals acquired by ultrasonic wave sensors. A given resolution corresponding to a minimum size of defects is also defined. This makes it possible firstly not to alert acceptable defects and secondly to give a stop point to the algorithm.

At step E2 the processing means 7 are configured to construct a grid on the image 13 in a plurality of current subdivisions. The dimensions of the subdivisions are selected according to the size of the object so that it is possible to have close neighbours and distant neighbours.

Figure 3A:
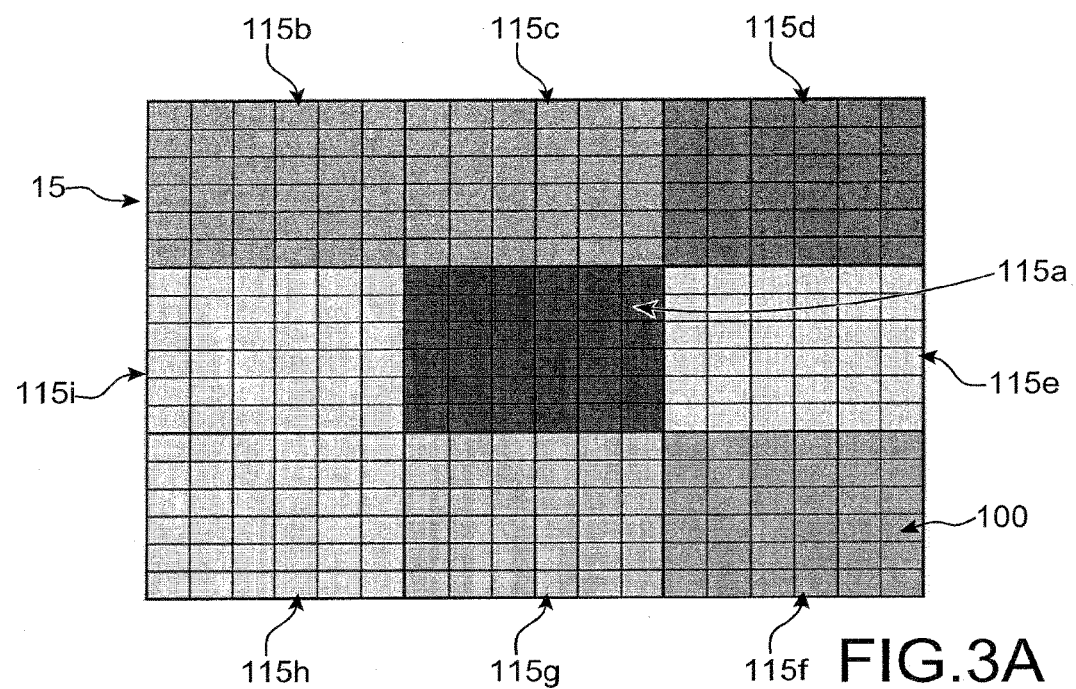
FIGS. 3a-3e are grids on an image illustrating schematically the steps of the flow diagram in FIG. 2.

FIG. 3A shows a grid 15 on a part of the image 13 in nine subdivisions 115a-115i in the form of large squares with the same sizes. The small squares 225 represent the resolution selected. Moreover, it should be noted that the subdivisions may also be hexagonal or triangular in shape or any other geometric shape.

At step E3 the processing means 7 are configured to calculate first current differentials between each current subdivision 115a and the adjacent current subdivisions 115b-155i. For example, the differential represents the difference in the values of a physical parameter (e.g. optical, thermal or audible field) between a subdivision and an adjacent subdivision.

More particularly, the processing means 7 calculate a component of the physical parameter relating to each subdivision and next compare the component of each subdivision with those of its neighbours.

According to the example in FIG. 3A, each square is compared with its eight neighbours by calculating the differential between firstly the component of the physical parameter in a square 115a and secondly the component relating to each of the eight neighbouring squares 115b-115i.

Step E4 is a test where the processing means 7 are configured to check whether or not there exists a current subdivision for which the first current differentials with at least a first given number of adjacent subdivisions indicate an abnormality.

An indicator of abnormality may for example be the comparison of the differential with a predetermined threshold. In a variant, the abnormality indicator may be defined by the difference between the observed differential and a sound differential measured during a learning phase and the comparison of this difference with a predetermined level. It should be noted that the predetermined threshold or level may depend on several factors such as for example the number of neighbours, the size of the subdivision 115a, the physical parameter measured, the required precision, etc.

If the result of the test of step E4 is negative, then it is considered at step E5 that the object 11 is valid.

On the other hand, if a subdivision is found for which the first current differentials, with at least a first given number of adjacent subdivisions, are indicative of an abnormality, then it is considered that this subdivision is potentially invalid and step E6 is passed to.

It should be noted that, if the differentials indicate an abnormality with only one other adjacent subdivision, it can probably be considered that it is a lack of precision or a measuring error. In other words, for the subdivision to be declared potentially invalid, it is necessary for there to be at least a threshold number of adjacent subdivisions with which the differentials are indicative of an abnormality. This threshold number may also depend on the number of neighbours, the size of the subdivision, the physical parameter measured, and the required precision. In the example in FIG. 3a, this threshold number is chosen to be equal to four and this figure shows that the subdivision 115a at the centre has a differential indicative of an abnormality with respect to at least four of its neighbours 115b-115i.

Thus, when the test of step E4 is confirmed, the processing means 7 are configured so as, at step E6, to compare the potentially invalid subdivision with distant subdivisions. In particular, the processing means 7 calculate second current differentials between the potentially invalid current subdivision and distant current subdivisions. For example, the dubious central square 115a in FIG. 3A can be compared with only eight distant neighbours (not shown) in order to limit the computing load. It should be noted that the neighbours are chosen differently for the subdivisions at the edges of the image since it is not possible to take neighbours in all directions. Thus, in order to take account of edge effects, it is possible to choose different thresholds depending on whether the potentially invalid subdivisions are at the edges or in the interior of the image.

Step E7 is a test where the processing means 7 are configured to check whether the current subdivision has, with at least a second given number of distant current subdivisions, second current differentials indicative of an abnormality. Neighbours that are sufficiently distant are taken in order to leave the potentially invalid zone. If the result of the test of step E7 is negative, then it is considered at step E8 that the dubious subdivision is valid. This is because, if a subdivision is different from its near neighbours but not from distant neighbours, it can be deduced that the subdivision in question is valid but not the near neighbours. In this case, a particular status can be envisaged but, in any event, the near neighbours will also be tested and detected by the algorithm.

On the other hand, if the result of the test of step E7 is confirmed, then it is considered at step E9 that the dubious subdivision is invalid.

As before, an abnormality is detected when the differential is above a predetermined threshold. Furthermore, for the dubious subdivision to be declared invalid, it is necessary for there to be at least a second given number of adjacent subdivisions with which the differentials are indicative of an abnormality. FIG. 3A also shows that the subdivision 115a at the centre has, with respect to at least four of its distant neighbours (not shown), a differential indicative of an abnormality.

Comparing the given subdivision with its near neighbours and next with distant neighbours makes it possible to confirm the invalidity of the subdivision and to adapt the resolution of the subdivisions. This is because, if the differentials between the given subdivision and the near neighbours are indicative of an abnormality and if the abnormality results from a real defect then the differentials with the distant neighbours must also indicate an abnormality given that they are distant from the defective area. In particular, if the abnormality is due to a progressive defect, then the differentials with distant neighbours are necessarily greater than with near neighbours. On the other hand, if the defect is very punctiform, then the differentials with distant neighbours are at least also as great as with near neighbours.

It should be noted that, in order to avoid false alarms, the same thresholds are not taken for near and distant comparisons. This is because distant subdivisions are normally sufficiently distant from the dubious area and therefore have fairly great differentials with respect to it. However, the context in the distant areas may be different and consequently the values of the physical parameter between the two areas may have significant differences without there necessarily being a defect. Thus, in order to avoid false alarms, it is advantageous to choose a greater threshold for a comparison between two distant subdivisions than for a comparison between two close subdivisions.

Next the processing means 7 are configured to compute other differentials by reorganising the subdivisions and/or refining their sizes.

Figure 3B:
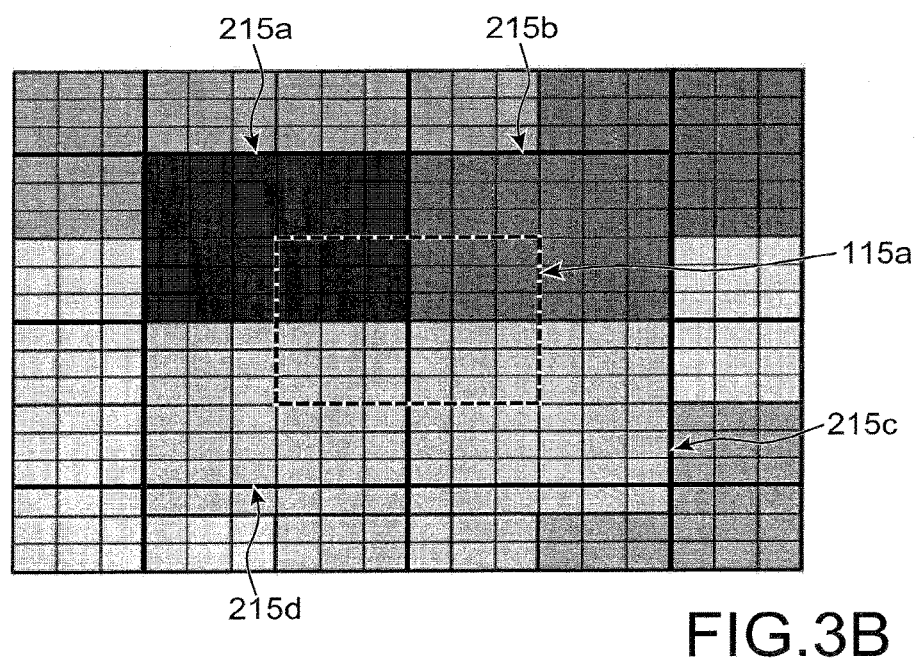

In fact, at step E10, the processing means 7 are configured to re-grid a zone 215 covering the subdivision 115a declared invalid (see FIG. 3B). Thus new subdivisions are formed that overlap the invalid subdivision. The new zone 215 is homothetic with respect to the invalid subdivision, for example with a ratio strictly between 1 and 2.

The example in FIG. 3B shows schematically a reorganisation of the subdivisions by a simple shifting by a half-square horizontally and a half-square vertically. Thus this example shows that four new current squares 215a-215d overlap the previous invalid current square 115a (shown in broken lines). Each of these four new squares 215a-215d covers a part of the previous square 115a plus a part of the immediate vicinity of the latter. This makes it possible to scrutinise the entire vicinity of the area declared invalid.

Once again the processing means 7 compute new differentials relating to the new division of the comparison areas.

This is because the new subdivisions 215a-215d are considered to be the actual current subdivisions and for each of these new subdivisions steps E11-E17 are performed, which are equivalent to steps E3-E9 respectively.

Thus at step E11 the processing means 7 are configured so as to calculate first current differentials between each new current subdivision 215a-215d and adjacent current subdivisions.

Step E12 is a test where the processing means 7 are configured to check whether there exists a new current subdivision for which first current differentials with at least a first given number of adjacent subdivisions are indicative of an abnormality. If the result of the test of step E12 is negative, then it is considered at step E13 that the subdivision is valid, or otherwise it is considered that it is potentially invalid and step E14 is passed on to.

At step E14, the processing means 7 are configured so as to compare the new potentially invalid subdivision with distant subdivisions.

Step E15 is a test where the processing means 7 are configured to check whether the new current subdivision has, with at least a second given number of distant current subdivisions, second current differentials indicative of an abnormality. If the result of the test of step E15 is negative, then it is considered at step E16 that the dubious subdivision is valid. On the other hand, if the result of the test of step E15 is confirmed, then it is considered at step E17 that the new dubious subdivision is invalid.

Thus, at the end of step E17, there is at least one new invalid subdivision and a previous invalid subdivision. The example in FIG. 3B shows a new invalid current square 215a and a previous invalid square 115a. Cross-checking between the current and previous invalid squares gives more information on the location of the defect.

This is because, at step E18, the processing means 7 are configured to make a mask according to a logic AND operation between the previous invalid subdivisions 115a and the new subdivisions 215a-215d in the overlap area 215. This forms subdivisions 315a-315d with reduced sizes comprising at least one invalid subdivision 315a of reduced size (see FIG. 3C). These new subdivisions 315a-315d of reduced sizes are considered to be the actual current subdivisions.

At step E19 the processing means 7 are configured so as to check whether the size of the actual current subdivision 315a-315d is larger than the predetermined resolution 100. If so, the processing means 7 are configured so as to reiterate the previous steps E3-E18 for each actual current subdivision, and otherwise the invalid current subdivision or subdivisions are declared at step E20 to be an abnormal subdivision or subdivisions.

Figure 3C:
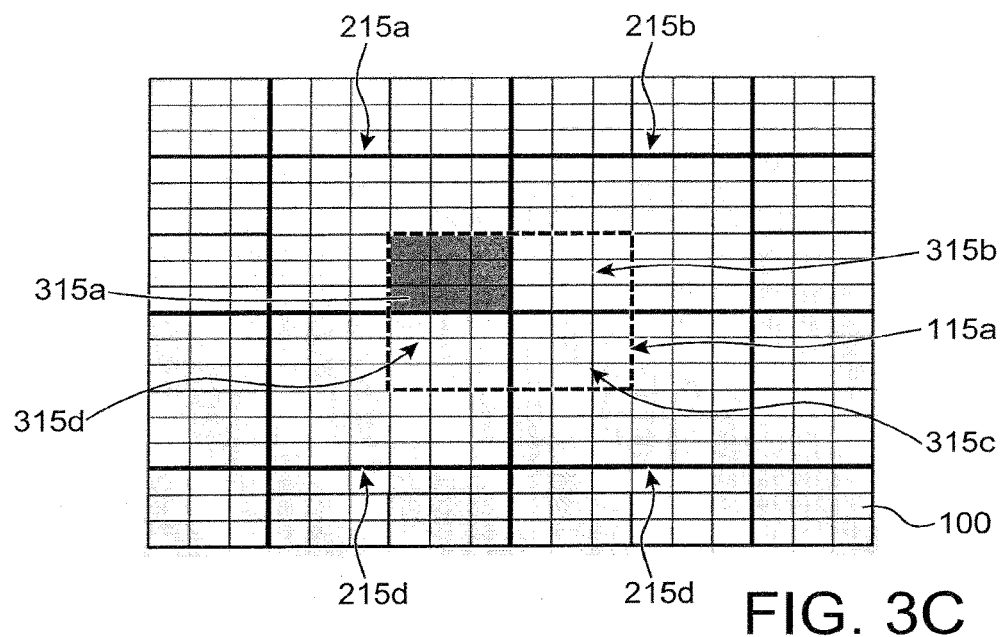
Figure 3D:
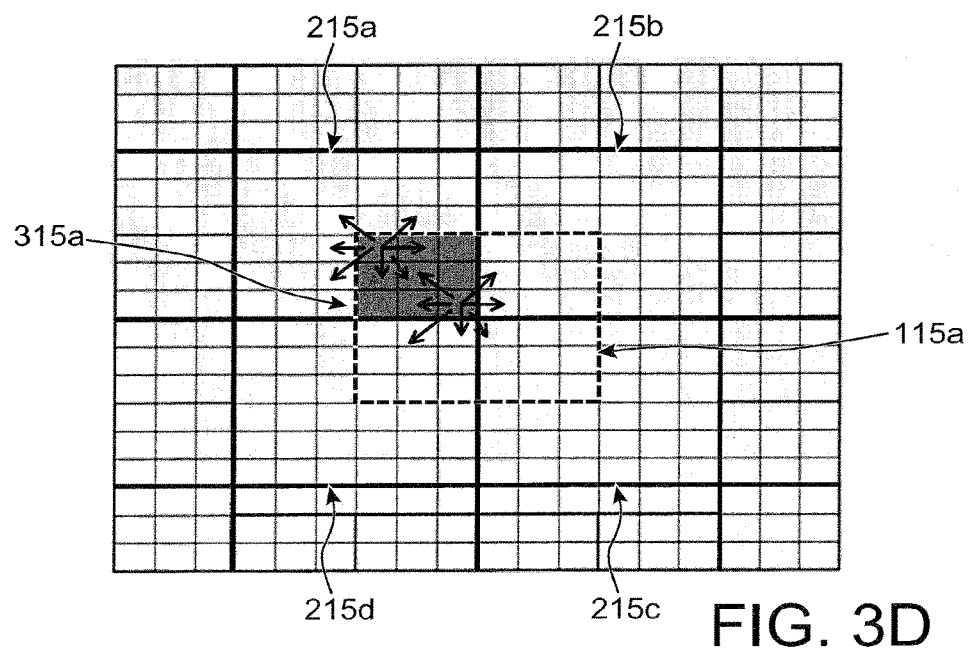
Figure 3E:
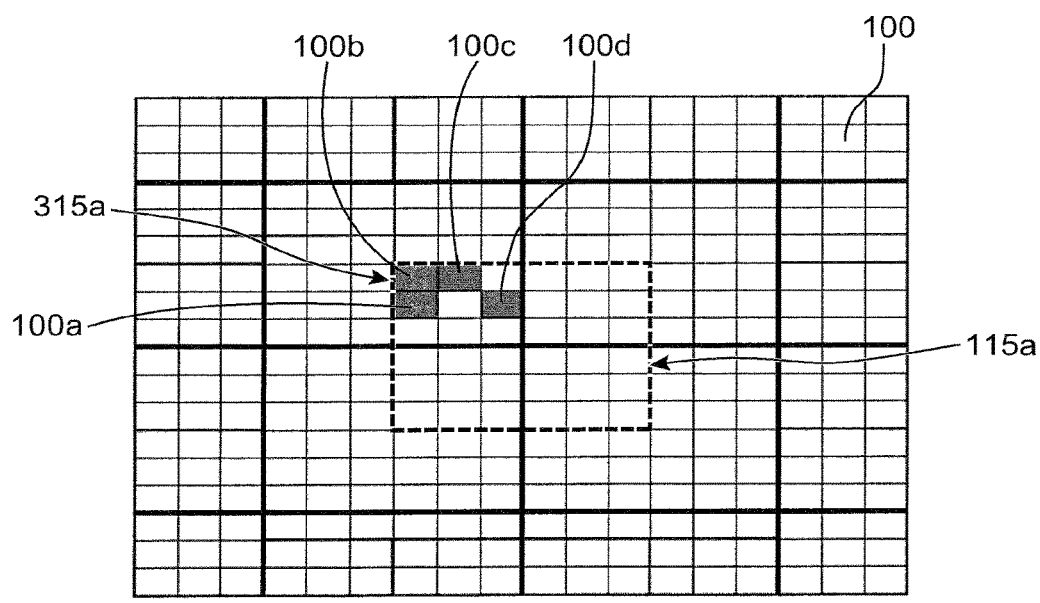

FIG. 3C shows that the mask AND refines the zone by reducing the length and width of the square by a factor of 2. However, the size of the invalid square 315a remains greater than the size of the small square 100 corresponding to the resolution and consequently the same steps are recommenced as illustrated in FIG. 3D. Finally, FIG. 3E shows that the resolution 100 is reached and the small invalid squares 100a-100d are located.

The example in FIGS. 3A-3E shows that the detection method according to the invention makes it possible to greatly reduce the number of computing steps.

This is because the image according to the example in FIGS. 3A-3E comprises 18×18=324 small boxes 100. Thus, by ignoring the edge effects, if each box 100 were compared with its eight adjacent boxes, there would be 2592 comparisons and the technique would be less effective since only abnormalities highly located on a box 100 would be detected.

With the above technique and still ignoring the edge effects, 9×8=72 comparisons are made at the step in FIG. 3A, 4×8=32 comparisons at the step in FIG. 3B, zero comparisons at the step in FIG. 3C, and finally 9×8=72 comparisons at the step in FIG. 3D, that is to say in total only 176 comparisons. This reduces the computing time and the load on the computer.

More generally, for an image of an object of 100 cm×20 cm and a resolution of 1 mm, if each area of 1 mm were taken independently and compared with its eight neighbours, there would be, without counting the edge effects, 1,600,000 comparisons and it is possible to detect only defects of 1 mm or very marked defects.

However, by applying the detection method according to the invention, taking an initial grid of 1 cm and assuming that there is only one defect, the total number of comparisons is approximately 16,000.

Thus the method according to the invention considerably reduces the number of calculations by optimising the number of comparisons. In addition, it makes it possible to detect defects the size of which lies between the dimensions of an initial subdivision 115a and the resolution 100 selected.

In fact FIGS. 4A-4D illustrate the detection of punctiform gradual defects on various grids.

FIGS. 4A and 4B show that a punctiform defect 21a can be detected on a large square 425 or on a small square 525. However, FIGS. 4C and 4D show that a gradual defect 21b can be detected on a large square 425 but not on a small square 525. This is because the differential between a small square 525 and its neighbours is very small and thus a gradual defect would not be detected with a conventional method, which considers only small squares.

Figure 5:
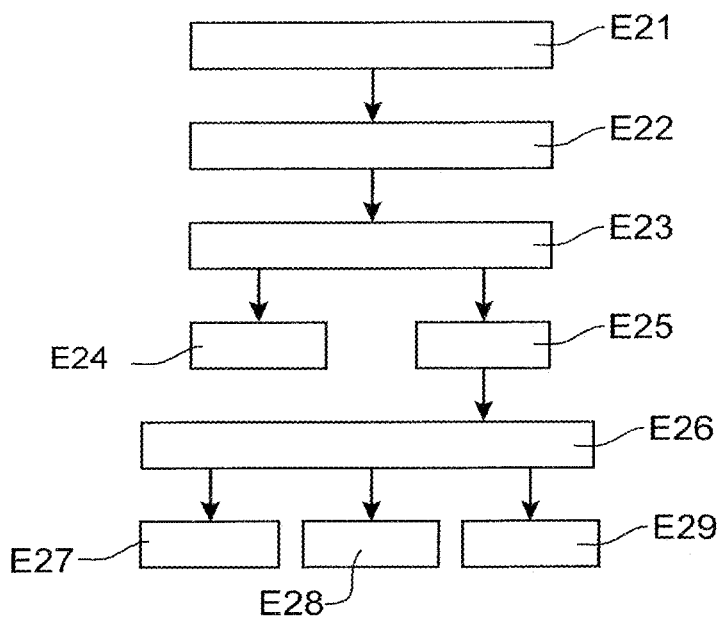
FIG. 5 is as a detection algorithm comprising a confirmation phase according to a first embodiment of the method, according to the invention.

FIG. 5 is a detection algorithm according to the invention comprising a confirmation phase according to a first embodiment.

The confirmation phase comprises a comparison of the differentials relating to an abnormal subdivision belonging to a last image with differentials relating to the same abnormal subdivision belonging to each of a given number of previous images of the object, the data on the previous abnormal subdivisions being recorded in a database 17 associated with the processing means.

Step E21 concerns the measurement or acquisition of a physical parameter (e.g. optical, thermal or audible field) relating to the object 11, making it possible to form an image 13 of the object 11.

At step E22, the data related to the physical parameter are sent to the processing means 7.

At step E23, the processing means 7 are configured so as to process the data in accordance with the flow diagram in FIG. 2.

In particular, at steps E4 and E12 (FIG. 2), it is checked whether the first current differentials are higher than a first predetermined threshold. Likewise, at steps E7 and E15 (FIG. 2), it is checked whether the second current differentials are higher than a second predetermined threshold. It should be noted that the values of the first and second thresholds may be modified according to the size of the subdivision and therefore the rank of the iteration. For example, at the first iteration, the detection is chosen so as to be fairly sensitive (i.e. low thresholds) in order to make it possible to identify any abnormal subdivisions. This is because, if the subdivision is large, normal and abnormal zones inside the subdivision will if necessary be averaged.

At the end of step E23, if no defect is found, then at step E24 the database 17 concerning the last detections is reset to zero.

On the other hand, if at the end of step E23 one or more abnormal subdivisions are detected, then at step E25 the information concerning the last abnormal subdivision or subdivisions are recorded in the database 17 before going to step E26.

At step E26, the processing means 7 are configured so as to compare the differentials relating to the abnormal subdivision or subdivisions belonging to the last image with differentials relating to the same abnormal subdivision or subdivisions belonging to each of the previous images of the object 11.

If it is found that the image 13 has an abnormality for the first time, then no alert is generated (step E27).

On the other hand, if it is found that the differentials have increased during the last images, then a high-importance alert is generated (step E28). A supplementary alert level can be added to follow the trend of the differentials. For example, a very high importance alert is generated if the differentials increase and the extrapolation shows, at a given time period (e.g. 10 flights), that a predetermined limit threshold has been exceeded.

Finally, if it is found that the differentials remain constant over the last images, then a medium-importance alert is generated (step E29).

Moreover, various threshold levels corresponding to various alert levels can be allocated.

Figure 6:
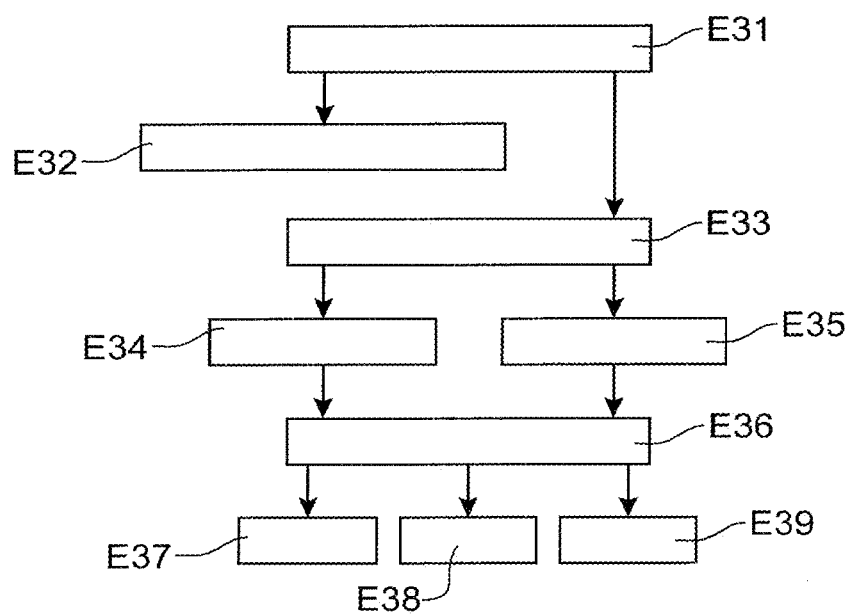
FIG. 6 is a detection algorithm comprising a confirmation phase according to a second embodiment of the method, according to the invention.

FIG. 6 is a detection algorithm according to the invention comprising a confirmation phase according to a second embodiment.

The steps of the algorithm of FIG. 6 are identical to those of FIG. 5 except for steps E32 and E33.

As before, step E31 concerns the measurement or acquisition of a physical parameter (e.g. optical, thermal or audible field) relating to the object 11 enabling an image 13 of the object to be formed. If the data correspond to a first image, then step E32 is passed to, and otherwise to step E33.

Step E32 is a learning phase during which a learning database is constructed by comparing the differentials of the subdivisions of the first image of a sound object. This may be done according to the steps of comparisons between adjacent subdivisions in the flow diagram in FIG. 2.

Thus, at step E32, a learning database recording sound differentials between various subdivisions of the original sound image are constructed, knowing that the latter is not necessarily uniform because of the intrinsic but normal differences in the object.

If the image of the object is not a first image, then step E33 is passed to, where the processing means 7 are configured so as to process the data in accordance with the flow diagram in FIG. 2.

However, at steps E4 and E12 (FIG. 2), the differences between the first current differentials of the adjacent subdivisions and the corresponding sound differentials are calculated in order to check whether they are higher than a predetermined level. At steps E7 and E15 (FIG. 2), it is checked whether the second current differentials between distant subdivisions and corresponding sound differentials are higher than a second predetermined threshold.

The detection method of the present invention is inexpensive in terms of computing resources and can therefore be easily implemented by onboard processing means installed in an aircraft in order for example to detect defects or incipient failure of a rotating element of an aircraft engine.

FIG. 7 illustrates schematically a system for detecting defects on a rotating element of an aircraft engine, according to a first embodiment of the system in FIG. 1.

The rotating element 111 is visible from the outside and corresponds for example to a vane or blade of a bladed wheel 112 or to a rotating cowl of the engine 114. The bladed wheel 112 may belong to a compressor of the engine 114 and may for example correspond to a faired or non-faired fan of the aircraft engine.

According to the embodiment in FIG. 7, the signals relating to the rotating element are infrared signals coming from the element and consequently the excitation means are onboard heating means 113 and the acquisition means are onboard thermographic means 115.

The heating means 113 are intended to heat the rotating element 111 of the engine 114 through thermal stressing 119. Naturally the heat penetrates the material of the rotating element 3. Thus the local temperatures will vary from one region to another since the heat will penetrate to a greater or lesser extent according to the presence or not of defects 121. By way of example, the heating means 113 may consist of one or more thermal emitters fixed to the engine 114 or the aircraft 116 opposite the rotating element 111. Thus each thermal emitter 113 remains permanently on the aircraft 116 and can be adjusted in order to heat the rotating element 121 periodically or in a pulsed fashion.

Moreover, the thermographic means 115 are intended to acquire at least one infrared image 113 and the rotating element 111 representing, following the thermal stressing 119 of the heating, a transient thermal field. It should be noted that the thermographic means 115 may consist of one or more thermal cameras fixed to the engine 114 or the aircraft 116 opposite the rotating element 111.

Advantageously, the rotating elements 111 are filmed during a rotation and at very low speed (that is to say at the beginning of the starting phase, the end of the stop phase or during "windmilling" functioning on the ground). This makes it possible to have a complete view of the rotating elements 111 without interfering with the acquisition of the images 113. The advantage of filming at low speed is the use of a single camera for detecting defects on all the blades, one after the other. It is of course possible to film at rest but in this case a plurality of cameras are needed to detect defects on all the blades.

It should be noted that heating and the acquisition of images have the advantage of being able to be done without contact, which makes it possible firstly not to damage the equipment being tested and secondly not to have sensors to place on the vanes 111 or very close to the vanes, which could disturb their aerodynamics. Furthermore, the fact that the heating 113 and thermographic 115 means are installed onboard makes it possible to acquire images 113 at each flight, automatically, without lengthy and expensive human intervention.

The processing means 107 are configured so as to acquire the infrared image 113 from the thermographic means 115 and to implement the steps of the detection method according to the flow diagrams in FIG. 2, 5 or 6.

The differentials can be calculated in relation to a component (for example, the amplitude or phase) of the thermal field between various subdivisions of the infrared image 113. The detection of the variations in the component of the thermal field is indicative of defects in or incipient rupture of the rotating element 111. Thus it is possible to monitor the rotating elements 111 of the engine 114 at each flight and automatically in order to detect the first signs of fatigue before a loss of blade occurs. In particular, the detection system 101 is well suited to monitoring the rotating elements 111 made from composite materials, which may suffer fatigue giving rise to defects 121 that are not visible on their surfaces.

It should be noted that analysing the data according to differential measurements on transient thermal phases makes it possible to be free from the context such as the external temperature or illumination by the sun. This is because the external conditions act in the same way on a current subdivision at two successive instants.

Advantageously, the processing means 107 of a computer 118 installed in the aircraft 116 or in a computer 118 integrated in the aircraft engine 114 of the EMU (Engine Monitoring Unit) type can be used for exploiting the detection system 101 according to the invention. In particular, the computer 118 can be used to execute a computer program recorded in storage means 117 of the computer 118 and comprising code instructions for implementing the detection method according to the invention.

It should be noted that the data acquired can be directly processed during the flight of the aircraft. In a variant, the data can be processed after the aircraft lands in order not to overload the computer 118 during flight. According to yet another variant, the data acquired can be transmitted to the ground in order to be processed by a computing station.

According to a first variant of the embodiment in FIG. 7, the heating means 113 are intended to heat the rotating element 111 by means of thermal pulses or transient thermal phases.

The heating means 113 correspond to a thermal emitter (for example a heating lamp) fixed directly to the engine of the aircraft, opposite the rotating element 111, in order to heat the latter in a pulsed manner. The rotating element is then heated in a sufficiently short time (a few milliseconds) for the material of the rotating element not to reach a constant temperature. The thermal emitter is fixed at a predetermined distance from the rotating element that may vary from a few millimeters to a few meters.

The thermographic means 115 correspond for example to a thermal camera installed close to the rotating element for example, between a few centimeters and a few meters, and acquire the images during heating.

In this case, the processing means 107 are configured so as to compute differentials between an amplitude of the thermal field (that is to say the temperature) of a current subdivision and amplitudes (that is to say temperatures) of the thermal fields of the adjacent subdivisions. Thus, if the material of the rotating element has a defect on the surface or in depth, the temperature at the surface following the pulsed thermal stressing will be different. Comparing the temperatures between the various subdivisions then makes it possible to detect defects.

According to a second variant of the embodiment in FIG. 7, the heating means 113 are intended to heat the rotating element 111 by means of periodic thermal waves for a given time, for example around a few seconds. In this case, a thermal emitter 113 is fixed to the engine (or the aircraft) opposite the rotating element 111 at a predetermined distance that may vary from a few millimeters to a few meters. The thermal emitter 113 is for example a heating lamp of the flash type sending a periodic thermal wave with a predetermined frequency to heat the rotating element periodically.

A thermal camera 115 is installed close to the rotating element 111, for example between a few centimeters and a few meters and acquires the images during heating.

The heat emitter 113 and the thermal camera 115 may be placed directly on the fuselage or the wings of the aircraft.

In this second variant, the processing means 107 are configured so as to carry out for example a Fourier analysis in order to determine the phase variation between the various subdivisions of the infrared image of the rotating element. If the material is uniform, the thermal energy is distributed identically and there is no phase difference between the various areas. On the other hand, if the material of the rotating element has a defect, the thermal energy will not propagate identically and the thermal wave will be either accelerated or slowed down in the defect, which will result in a phase difference. Thus the processing means 107 compute the phase differences between the thermal field of a current subdivision and the thermal fields of the adjacent subdivisions in order to detect the defects.

It should be noted that this second variant has the advantage of being little influenced by the distance of the heat source or illumination from the sun since it is not the temperature but the phase difference that is measured. In order to increase the precision of the measurements, it is preferable for the heat emitter not to be too far away from the rotating element.

According to a third variant of the embodiment in FIG. 7, the heating means 113 consist of at least one anti-frost heating element already existing in the engine.

This is because, if the rotating elements 111 already have heating means intended to prevent frost, the detection system of the present invention may cleverly use this heat source and it is therefore possible to omit the installation of supplementary heating means and consequently reduce the onboard mass.

In this case, the anti-frost heating element is adjusted, during autotests on starting for example, so as to provide heat during predetermined periods.

If the heating element is not integrated in the vane but fixed outside, then the detection process is strictly identical to that of the first and second variants. On the other hand, if the heating element is sufficiently powerful and is integrated in the vane, a relatively short heating time of a few seconds followed by a cooling time of a few seconds may be used.

More particularly, if the heating element consists for example of heating wires distributed over the surface of the vane, the heating element is supplied with a constant current intensity during a given heating time and then heating is stopped in order to reduce the temperature. After a given waiting time (always identical from flight to flight), there is then a transient phase of the thermal field and the processing means 107 trigger the camera in order to take an infrared photograph. In the event of abnormality in the materiel of the rotating element, the cooling will be different and it is then possible to compare each subdivision with its near and far neighbours, from flight to flight. On the other hand, in this case, it is not possible to detect defects under the wires since their temperature would falsify the thermal response of the material at this point.

On the other hand, if the heating wires are not on the surface but integrated within the material of the vane, the situation is more favourable than before since the wires do not conceal any surface of the blade and there is access directly to the response in thickness and it is then possible to detect internal defects and over the entire surface of the vane. The processing of the data is the same as that detailed above.

Furthermore, the processing means 107 are advantageously configured so as to verify the correct functioning of the anti-frost heating element by monitoring the amplitude differential of the rotating elements. Thus, if the amplitude response is lower and lower or even zero or higher and higher from flight to flight even considering the effect of aging of the blades on the thermal responses, the processing means 107 may blame the heating element.

Figure 8:
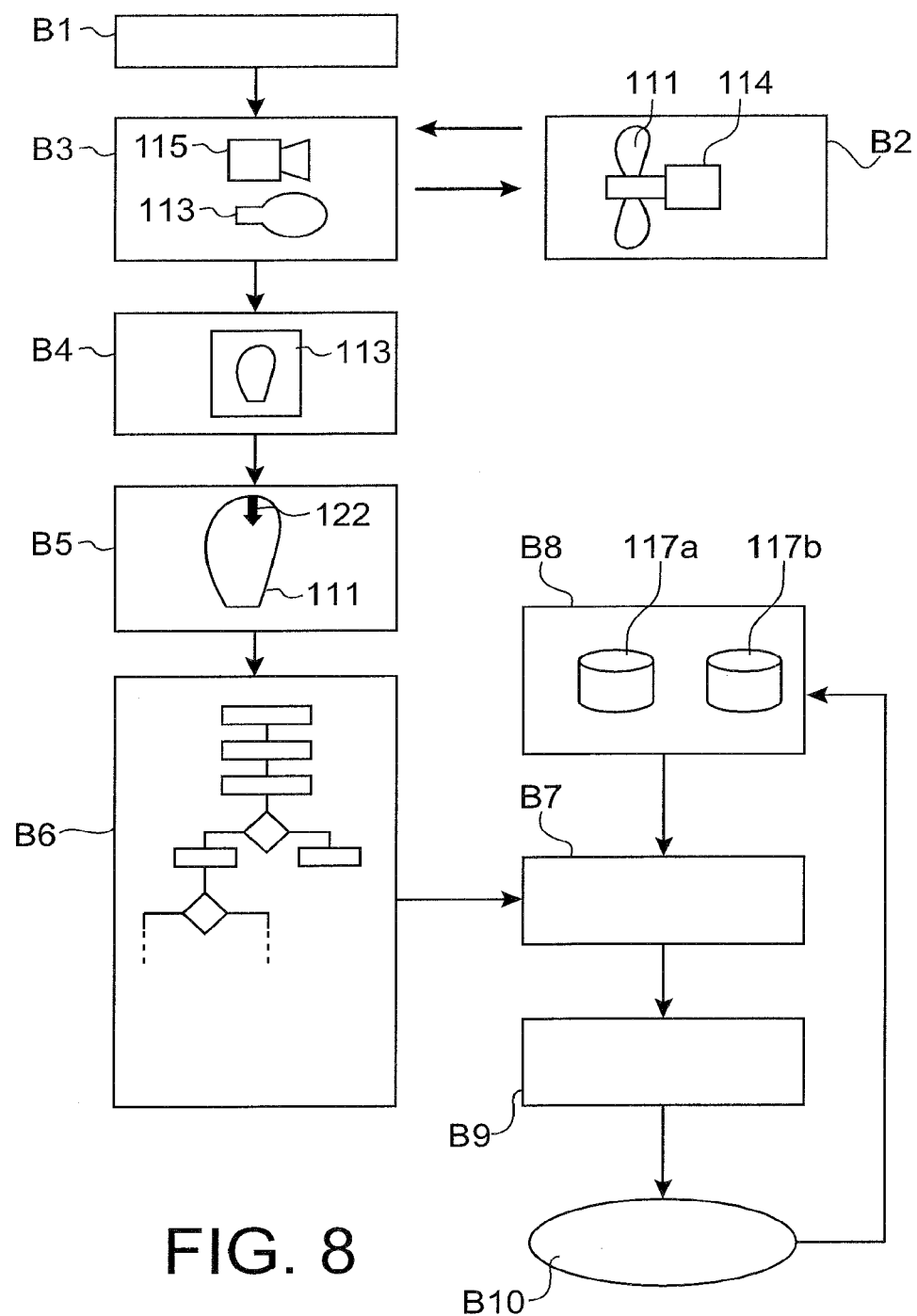
FIG. 8 is a block diagram illustrating the steps of detecting the defects on a bladed wheel of an engine, according to the system in FIG. 7.

FIG. 8 is a block diagram illustrating the steps of detecting defects on a bladed wheel of the engine in accordance with the system in FIG. 7.

According to this example, the rotating element 111 corresponds to each of the vanes of the bladed wheel 112.

At block B1, the processing means 107 receive data from the engine 114 (represented by the block B2), concerning the speed of rotation of the bladed wheel 112 to be monitored. The processing means 107 trigger the detection method when the bladed wheel 112 begins to rotate at very low speed.

At block B3 the heating means 113 heat the blades 111 of the bladed wheel 112 of the engine 114 (block B2) by thermal stressing 119 generating a thermal field that changes according to the heating and cooling phases. It should be noted that the thermal stressing (a thermal pulse or a periodic thermal wave) penetrates the material of the vane 111 so that, if the material has a defect 121 (on the surface or in depth), the amplitude and/or phase of the thermal field on the surface will be different.

Next, while the thermal field is in its transient heating or cooling phase, the thermal camera or cameras 115 film the vanes 111 of the bladed wheel 112 of the engine (block B2) in order to acquire at least one infrared image 113 of the vanes 111. Thus, at block B4, at least one infrared image 113 is generated. It should be noted that each thermal camera 115 may be configured so as to acquire one image per vane or a single image for all the vanes on the bladed wheel 112.

At block B5, the means 122 for identifying the vanes 111 are used to distinguish the various vanes on the bladed wheel 112. This makes it possible to monitor the various vanes over time and to identify the one or ones that have defects.

These identification means are for example optical shape recognition means. It is possible for example to use the thermal camera 115 itself coupled to a shape recognition algorithm in order to identify the vanes.

In a variant, the identification means are means of individualisation by a marking 122 or labelling on one or two vanes 111 of the bladed wheel 112. It is possible to individualise the vanes 111 by numbering them with paint or any other material inserted in the vane or disposed on its surface.

At block B6, the processing means 107 perform the steps of the flow diagram of FIG. 2, 5 or 6. In particular, the processing means 107 carry out for example a Fourier analysis in order to calculate a component (the amplitude or phase) of the thermal field of each subdivision of the infrared image 113 for each of the vanes 111 and compare the various subdivisions with each other.

More particularly, when a thermal pulse is used to heat the vanes 111 of the bladed wheel 112, then the component of the thermal field is the amplitude of the thermal field (that is to say the temperature). On the other hand, when a periodic thermal wave is used for heating the vanes 111, then the component of the thermal field is the phase of the thermal field.

If the material of the vane is uniform, its entire surface responds identically to the thermal stressing 119 and consequently the component of the thermal field is constant over all the zones. On the other hand, if the material has roughness on the surface or in depth, the component of the thermal field on the surface following the thermal stressing 119 will be different. Thus, by comparing the components on various relatively close zones, it is possible to detect defects.

When a defect is detected at block B7, then, before sending the alert, the processing means 107 compare at block B7 the results on several flights, in order to determine whether the abnormality is still being detected (see also steps E26-E29 and E36-E39 of FIGS. 5 and 6). This is because the processing means 107 are configured so as to record at each flight the differentials relating to the thermal fields of the various subdivisions in order to analyse the change in these differentials from flight to flight. Thus it is possible to quantify the change in the defects for each vane 111 by comparing the data issuing from the current flight with data from the previous flights stored in a database 117*a* (block B8).

Advantageously, the detection system 101 comprises a library of abnormalities or a database 117*b* (block B8) of signatures of deteriorations representing various forms of deterioration and their states of advancement. This enables the processing means 107 to compare the differentials relating to the thermal fields of the regions having incipient failure with the characteristics of deteriorations and thus rule on the type of deterioration and on the state of advancement thereof.

FIG. 9 illustrates schematically a system for detecting defects on a rotating element of an aircraft engine, according to a second embodiment of the system in FIG. 1.

According to this embodiment, the signals relating to the rotating element are ultrasound signals coming from the rotating element and consequently the excitation means are means 213 for emitting ultrasonic waves and the acquisition means are means 215 for receiving ultrasonic waves reflected by the element 211.

The emission 213 and reception 215 means may form a single device. More particularly, the device may comprise an ultrasound source of the electrocapacitive or piezoelectric type coupled to a receiver of the same type (i.e. electrocapacitive if the source is electrocapacitive).

The emission 213 and reception 215 means are fitted and installed on the engine 214 by means of pivoting and/or rotation means 232. Thus the emission 213 and reception 215 means may pivot and/or rotate in order to sweep several regions in space, scanning for example each rotating element 211 of a bladed wheel 212. Thus it is not necessary to install an ultrasound emitting/receiving device on each blade. It should be noted that the rotating elements 211 are scanned when they are at rest.

Advantageously, the ultrasound source 213 produces ultrasound in the low range (for example [50 kHz-1 MHz]) in order to avoid excessive attenuation, which is a function of the square of the frequency. The frequency can be adapted according to the resolution required (i.e. the size of the defect sought). The higher the frequency the greater the resolution but the more attenuated the signal, and therefore a compromise must be found according to the application.

The processing means 207 are configured to form an image 213 representing the rotating element 211 from the ultrasonic waves 219 reflected by the element 211 and captured by the reception means 215 and to implement the steps of the detection method according to the flow diagrams in FIG. 2, 5 or 6.

The differentials can be calculated in relation to the intensity or direction of the ultrasonic waves 219 reflected. It should be noted that the ultrasonic waves penetrate the material very little and will therefore be reflected to the extent of more than 99.9% (because of the difference in acoustic impedance between air and metals or composite materials). Thus, in the event of any abnormality or surface defect, the reflection will be different in intensity and/or direction and it is then possible to detect small structural defects following for example an impact by a foreign body.

Thus the rotating elements 211 of the engine 214 can be monitored at each flight automatically in order to detect the first signs of fatigue before a loss of blade occurs.

It should be noted that analysing the data in accordance with differential measurements on intensities or directions of the reflected waves makes it possible to be free from the context such as the fact that the element being monitored may not always be at the same distance from the reception means.

The present invention also makes it possible to monitor the rotating elements made from metal or composite materials of an aircraft engine in order to detect the first signs of fatigue using means fixed to the engine or the aircraft, at each flight, automatically, and individually. It advantageously applies to monitoring the blades of the fan of a turbofan, the propellers of a turboprop engine or of an open rotor, and the rotating cowls of the latter.

The invention claimed is:

1. A method for detecting defects on an object, comprising the following steps:
    forming an image representing said object from signals relating to the object,
    constructing subdivisions of said image according to auto-adaptive resolutions comprising a comparison of a given subdivision with its near neighbors and next with distant neighbors, said resolutions iteratively adapting to the extent of the defect, and
    iteratively calculating differentials of the various subdivisions in order to detect an abnormal subdivision indicative of incipient failure.

2. The method according to claim 1, comprising a confirmation phase comprising a comparison of the differentials relating to an abnormal subdivision belonging to a last image with differential relating to the same abnormal subdivision belonging to each of a given number of previous images of said object.

3. The method according to claim 2, comprising:
    generating an alert of high or very high importance when the differentials have increased during the last images, and
    generating an alert of medium importance when the differentials remain constant during the last images.

4. The method according to claim 1, wherein the steps of constructing the subdivisions and calculating of the differentials comprise:
- constructing a grid on said image in a plurality of current subdivisions,
- calculating first current differentials between each current subdivision and adjacent current subdivisions,
- checking whether there exists a current subdivision for which first current differentials with at least a first given number of adjacent subdivisions indicate an abnormality,
- calculating, should the previous step be confirmed, second current differentials between said current subdivision and distant current subdivisions,
- checking whether said current subdivision has, with at least a second given number of distant current subdivisions, second current differentials indicating an abnormality,
- declaring said current subdivision to be invalid should the previous step be confirmed,
- reconstructing a grid on a region covering said invalid current subdivision in order to form new subdivisions overlapping the previous invalid subdivision, the new subdivisions being considered to be the actual current subdivisions,
- repeating steps for each of the new current subdivisions of said overlap zone,
- making a mask according to a logic AND operation in said overlap zone between the previous invalid subdivisions and the new subdivisions, thus forming subdivisions with reduced sizes, said subdivisions with reduced sizes being considered to be the actual current subdivisions,
- checking whether the size of the actual current subdivision is greater than a predetermined resolution, and
- reiterating, should the previous step be confirmed, the previous steps for each actual current subdivision, or otherwise declaring the invalid current subdivision or subdivisions to be an abnormal subdivision or subdivisions.

5. The method according to claim 4, comprising checking whether the first current differentials are higher than a first predetermined threshold, and whether the second current differentials are higher than a second predetermined threshold.

6. The method according to claim 4, comprising constructing a learning database recording sound differentials between various subdivisions of the image, and calculating first differences between the first current differentials and the corresponding sound differentials in order to check whether the first differences are higher than a predetermined level, and calculating second differences between the second current differentials and the corresponding sound differentials in order to check whether the second differences are higher than a second predetermined level.

7. The method according to claim 1, wherein said object is a rotating element of an aircraft engine.

8. The method according to claim 1, wherein the signals relating to said object are infrared signals coming from the object so that said image representing said object is an infrared image representing a transient thermal field after heating of the object by thermal stressing.

9. The method according to claim 1, wherein the signals relating to said object are ultrasound signals coming from the object so that said image representing said object is an image representing ultrasound waves reflected by the object.

10. A system for detecting defects on at least one rotating element of an aircraft engine, said system comprising:
- onboard excitation means installed so as to cause the emission of signals by said rotating element,
- onboard acquisition means installed so as to acquire the signal sent by said rotating element, and
- processing means configured so as to perform the steps of forming an image representing said rotating element from signals relating to the rotating element, constructing subdivisions of said image according to auto-adaptive resolutions comprising a comparison of a given subdivision with its near neighbors and next with distant neighbors, said resolutions iteratively adapting to the extent of the defect, and iteratively calculating the differentials of the various subdivisions in order to detect an abnormal subdivision indicative of incipient failure.

11. The system according to claim 10, wherein the excitation means are heating means for heating said rotating element of the engine with a thermal stressing, and wherein the acquisition means are thermographic means for acquiring an infrared image representing a transient-phase thermal field of said rotating element.

12. The system according to claim 10, wherein the excitation means are means for emitting ultrasonic waves, and wherein the acquisition means are means for receiving ultrasonic waves reflected by the object.

* * * * *